(12) United States Patent
Kumar et al.

(10) Patent No.: US 9,765,411 B2
(45) Date of Patent: Sep. 19, 2017

(54) GREEN PROCESS TO HYDROLYZE CARBOHYDRATES FROM TOBACCO BIOMASS USING SUBCRITICAL WATER

(71) Applicant: TYTON BIOSCIENCES, LLC, Danville, VA (US)

(72) Inventors: Sandeep Kumar, Virginia Beach, VA (US); Jose Luis Garcia Moscoso, Norfolk, VA (US); Iulian Bobe, Danville, VA (US); Peter Majeranowski, Danville, VA (US)

(73) Assignee: Tyton Biosciences, LLC, Danville, VA (US)

( * ) Notice: Subject to any disclaimer, the term of this patent is extended or adjusted under 35 U.S.C. 154(b) by 140 days.

(21) Appl. No.: 14/270,839

(22) Filed: May 6, 2014

(65) Prior Publication Data

US 2014/0331993 A1 Nov. 13, 2014

Related U.S. Application Data

(60) Provisional application No. 61/820,446, filed on May 7, 2013.

(51) Int. Cl.
*C13K 1/02* (2006.01)
*C07D 401/04* (2006.01)
*A24B 15/24* (2006.01)

(52) U.S. Cl.
CPC ............... *C13K 1/02* (2013.01); *A24B 15/24* (2013.01); *C07D 401/04* (2013.01)

(58) Field of Classification Search
CPC ....................................................... C13K 1/02
See application file for complete search history.

(56) References Cited

U.S. PATENT DOCUMENTS

| 6,419,788 | B1 * | 7/2002 | Wingerson | D21C 1/02 127/37 |
| 8,323,923 | B1 * | 12/2012 | Horton | C12P 7/06 435/161 |
| 2007/0014912 | A1 | 1/2007 | Mazza et al. | |
| 2010/0175690 | A1 * | 7/2010 | Nagahama | C07H 3/02 127/37 |
| 2012/0301928 | A1 * | 11/2012 | Bae | C10L 1/023 435/99 |

(Continued)

FOREIGN PATENT DOCUMENTS

WO  WO 2013/165308  * 11/2013

OTHER PUBLICATIONS

A comparison of liquid hot water and steam pretreatments of sugar cane bagasse for bioconversion to ethanol. Mark Laser et al. Bioresource Technology, V. 81, pp. 33-44, 2002.*

(Continued)

*Primary Examiner* — Douglas B Call
(74) *Attorney, Agent, or Firm* — NK Patent Law, PLLC (57) ABSTRACT

Processes for recovering sugars and nicotine from a tobacco biomass include feeding a biomass of tobacco plants and subcritical water to a reactor, hydrolyzing the biomass of tobacco plants with the subcritical water at a temperature between about 150° C. and 305° C. and recovering a liquid product and a solid product from the reactor, wherein the liquid product contains water-soluble sugars and nicotine.

8 Claims, 6 Drawing Sheets

(56) References Cited

U.S. PATENT DOCUMENTS

| | | | |
|---|---|---|---|
| 2013/0206571 A1* | 8/2013 | Heilmann | B01D 9/0013 201/3 |
| 2014/0271951 A1* | 9/2014 | Mua | A24B 15/241 424/751 |
| 2014/0275299 A1* | 9/2014 | Bedwell | C07C 1/12 518/704 |
| 2015/0122245 A1* | 5/2015 | Johannesson | C13K 1/02 127/37 |

OTHER PUBLICATIONS

USPTO, Non-Final Rejection for U.S. Appl. No. 14/437,846, Sep. 17, 2015.

* cited by examiner

Puree solids compositional analysis

GREEN PROCESS TO HYDROLYZE CARBOHYDRATES FROM TOBACCO BIOMASS USING SUBCRITICAL WATER

CROSS REFERENCE TO RELATED APPLICATION

This application claims priority to U.S. Provisional Patent Application Ser. No. 61/820,446 filed on May 5, 2013, the entirety of which is incorporated herein by reference.

TECHNICAL FIELD

The embodiments herein relate in general to subcritical water hydrolysis methods to enhanced tobacco varieties for the economic production of sugars and oils for bioethanol, bio-based products, and liquid fuels production.

BACKGROUND

The corn to ethanol process is a matured technology and the enzyme (α-amylase and glucoamylase) needed for starch hydrolyses is commercially available. The production of ethanol becomes very difficult when lignocellulosic feed stocks (switchgrass, pinewood) are used. The sugars are locked in a very complex structure and so require costly enzymes to unlock the sugars. Among the research community, this is known as "recalcitrance" and such recalcitrance currently limits brewers to a 40% conversion of the energy content available in cellulosic feedstock to ethanol. If monomer sugars are readily available, the fermentation process, by contrast, converts about 90% of the energy in simple sugars to ethanol.

SUMMARY

Some of the major technological barriers identified in the full-scale commercialization of lignocellulosic biomass to bioethanol need important technological breakthroughs in the following areas:

Feedstock Development: The current feedstock cost is assumed to be $70-80/metric ton. However, the cost is likely to be location sensitive. It is important to critically estimate the feedstock cost, which may limit the plant locations to certain areas.

Lignin Utilization: Lignin is a complex aromatic polymer and provides considerable challenges in processing lignocellulosic materials for bioethanol. The combustion of lignin for process heat and power production is one of the major causes of lower thermodynamic efficiency (~35%) of the overall conversion process. The better or high value utilization of lignin (bioproducts) can improve the overall efficiency of the process.

Enzyme Cost: The development of inexpensive enzymes to ferment both 5 and 6 carbon sugars is a foremost necessity to reduce the production cost of ethanol for lignocellulosic feedstock. As per a recent study, the cost contribution of enzymes to ethanol produced by the conversion of corn stover was found to be $0.68/gal if the sugars in the biomass could be converted at maximum theoretical yields, and $1.47/gal if the yields were based on saccharification and fermentation yields.

In view of these challenges, a process is disclosed to use tobacco as a platform biomass for biofuels. Disclosed is novel feedstock selectivity combined with a water-based green process technology to produce fermentable sugars and tobacco oil from a naturally grown or genetically modified tobacco plants and tobacco stalks. The proposed systematic approach potentially addresses challenges with feedstock development, lignin utilization, and enzyme cost.

The embodiments herein disclose methods of using natural or a novel enhanced tobacco plant variety for producing fermentable sugars as well as oil/lipids using a unique and environmentally-friendly subcritical water hydrolysis process. Tobacco is the targeted biomass platform because it is a well-established non-food industrial crop that has a long 400-year tradition of cultivation in the United States and more than 120 other countries. This is important as farmers are generally wary of producing crops with no agricultural market history. Tobacco also has a well-established history for genetic modification and can yield a very high biomass per hectare.

Processes for recovering sugars from a tobacco biomass are provided. One process comprises feeding a tobacco stock and low temperature subcritical water to a reactor; hydrolyzing the tobacco stock with the low temperature subcritical water; recovering a first liquid product and a first solid product from the reactor; recycling the first solid product to the reactor with high temperature subcritical water; further hydrolyzing the solid product with the high temperature subcritical water; and recovering a second liquid product and a second solid product from the reactor, wherein the first liquid product and the second liquid product contain the sugars.

Processes for recovering sugars and nicotine from a tobacco biomass include feeding a biomass of tobacco plants and subcritical water to a reactor, hydrolyzing the biomass of tobacco plants with the subcritical water at a temperature between about 150° C. and 305° C. and recovering a liquid product and a solid product from the reactor, wherein the liquid product contains water-soluble sugars and nicotine.

BRIEF DESCRIPTION OF THE DRAWINGS

The various features, advantages and other uses of the present apparatus will become more apparent by referring to the following detailed description and drawing in which.

DETAILED DESCRIPTION

Subcritical water based green technology is disclosed for converting carbohydrates present in tobacco biomass to water-soluble sugars (oligomers and monomers) which will eliminate the use of cellulase enzymes traditionally used in lignocellulosic biomass hydrolysis. Further, the disclosed process is capable of fractionating lipids/oils and nicotine present in tobacco biomass during the proposed subcritical water hydrolysis. Nicotine is an alkaloid (a substance with a basic charge) found predominantly in tobacco, and in lower quantities in tomato, potato, eggplant (aubergine), and green pepper. The chemical name and formula of nicotine is 3-(1-Methyl-2-pyrrolidinyl)pyridine and $C_{10}H_{14}N_2$, respectively. Nicotine constitutes 0.3 to 3 percent of the tobacco plant by dry weight, with biosynthesis taking place in the roots, and accumulates in the leaves. Nicotine is a potent neurotoxin and has application in many insecticides. The disclosure is novel on following accounts:

Feedstock Selection: Use of genetically modified or non-modified and specialty selection tobacco to increase the accumulation of lipids in green biomass. This process can also be applied to extract sugar from tobacco stalks. The composition analysis shows that non-structural sugars in modified or unmodified tobacco leaves are comparable to that of energy crops (switchgrass, miscanthus) whereas lignin content in tobacco leaves is significantly low. The elemental analysis of tobacco leaves showed the carbon content in the range of 37-39 wt % and oil content was about 5 wt % on dry weight basis. More than 75 wt % of structural or non-structural sugars in tobacco biomass is available as glucose upon hydrolysis which is fermentable by the use of a commercially available *Saccharomyces cerevisiae*. It is important to note here that the fermentation of 6-carbon sugar (e.g. glucose) is relatively easier than 5-carbon sugar (e.g. xylose). A wide range of feedstock with ability to develop significant biomass can be processed using the disclosed method.

Feedstock Preparation: Feeding slurries at high pressure is always an engineering challenge but at large scale it is less of a problem where progressive cavity or similar commercially available pumps can be used. Tobacco biomass is relatively less fibrous and oily when compared to lignocellulosic biomass (e.g. switchgrass, corn stover) because of the presence of non-structural sugars and extractives. The moisture content in freshly-cut tobacco biomass ranges from 84 to 96 wt % which can be used for wet grinding. Therefore, engineering challenges associated with high pressure pumping of tobacco biomass slurry are not significant. To pump the tobacco biomass into a reactor, the tobacco mass can be wet grinded to make an easily pumpable 5-15 wt % puree.

Subcritical Water Hydrolysis of Tobacco Puree and Fractionation of Lipids/Oils: The modified tobacco leaves mainly contain biopolymers such as carbohydrates, oils, and a small amount of nicotine. These polymeric components have different hydrolysis rates in the subcritical water medium and also are very sensitive to residence time. This difference in hydrolysis rates can be utilized to hydrolyze carbohydrates to water-soluble oligomeric and monomeric sugars. Since nicotine is prone to be hydrolyzed along with sugars, the liquid fraction after subcritical water hydrolysis is expected to contain some soluble nicotine. In general, high conversion rates can be achieved at very short residence times (5 seconds to 15 minutes, as non-limiting examples) in a continuous process which can facilitate the design of a very compact reactor with high throughput. The disclosed novel process uses subcritical water based scalable technology for the fractionating of sugars and lipids/oils present in tobacco biomass in a very short residence time.

Figure 1:
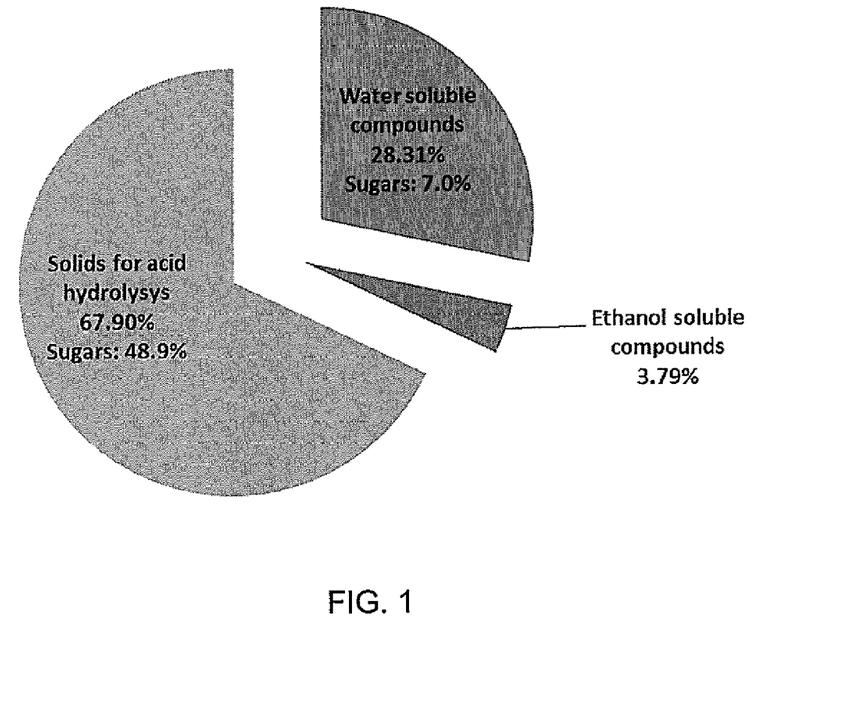
FIG. 1 is a graph showing the carbohydrates compositions present in one of the representative tobacco stems.

FIG. 1 shows the carbohydrate compositions present in one of the representative tobacco stems. Total sugar in this sample is 55.8 wt % on dry weight (DW) basis (7.67 wt % on fresh weight basis). It can be observed from the composition that stems contain 28.31 wt % of water-soluble compounds that can be extracted just by water using soxhlet extraction. It indicates that subcritical water at much milder conditions (<200° C.) can be used to hydrolyze these non-structural (free and amorphous) carbohydrates and extractives. The remaining structural sugars (~48.9 wt % (DW) shown in FIG. 1 can also be hydrolyzed with the use of subcritical water at a higher temperature between 200 to 350° C. under subcritical water conditions.

Figure 2:
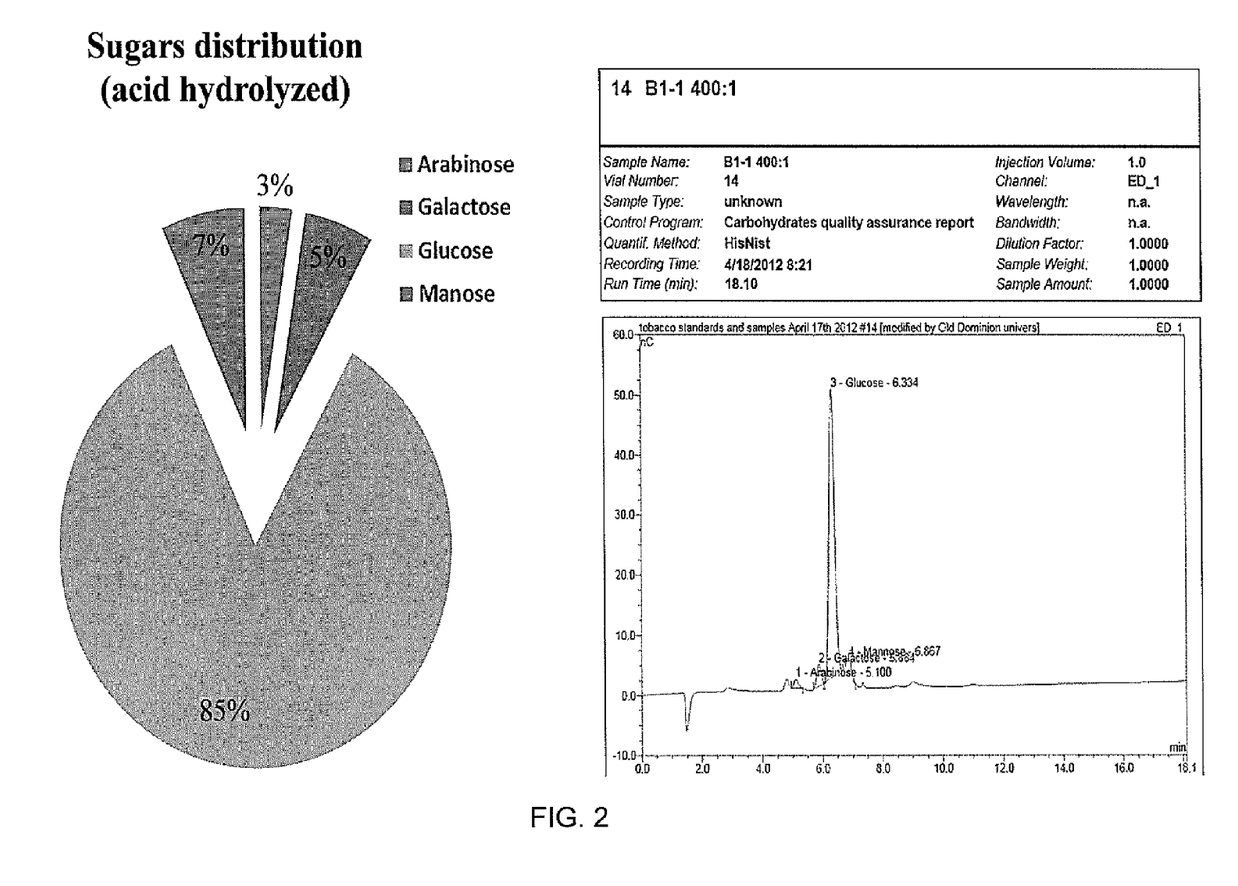
FIG. 2 is a graph showing the proportional distributions of sugar in acid hydrolyzed samples (structural sugars) of a typical tobacco biomass analyzed by ion chromatography (Dionex ICS-5000 model)

More than 75 wt % (DW) of sugars in tobacco biomass, depending upon the different parts of plant, is available as glucose upon hydrolysis. The proportional distributions of sugar in acid hydrolyzed samples (structural sugars) of a typical tobacco biomass analyzed by ion chromatography (Dionex ICS-5000 model) are shown in FIG. 2.

Figure 3:
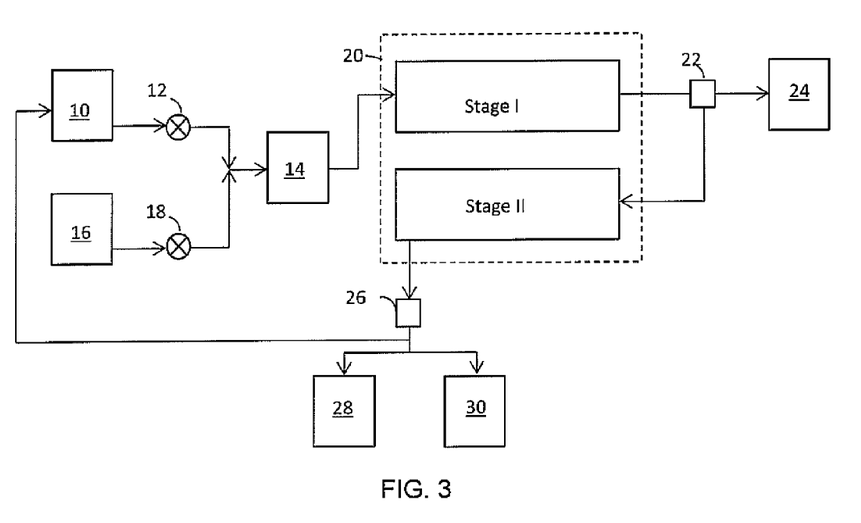
FIG. 3 is a schematic of a subcritical water hydrolysis process for tobacco biomass as disclosed herein.

The overall subcritical water hydrolysis processing scheme for tobacco biomass is represented in FIG. 3. Water from a water supply 10 is pumped via pump 12 to a mixer 14 and tobacco feedstock from a tobacco feedstock supply 16 is pumped via pump 18 to the mixer 14. From the mixer 14, the feed is provided to the reactor 20. Stage I and stage II are shown to simplify the process description. These stages can be integrated in the reactor 20, such as a single tubular reactor with multiple openings at different tube lengths, by maintaining a temperature gradient along the reactor 20. With a two-stage reactor, the pressure is controlled with pressure regulator 22. The effluent from Stage I is separated into a liquid product and a solid product. The liquid product 24 is collected, and the solid product is fed to Stage II. Stage II pressure is controlled with pressure regulator 26. The effluent from Stage II is separated into a liquid product 28 and a solid product 30. Water can be recycled back to the water supply 10. With a single stage reactor 20, no intermediate liquid product 24 is recovered.

Subcritical water is a non-toxic, environmentally benign and inexpensive media for chemical reactions. Liquid (hot compressed) water below the critical point (374° C., 221 bar) is referred as subcritical water. Ambient water is polar, has an infinite network of hydrogen bonding, and does not solubilize most organics. As water is heated, the H-bonds start weakening, allowing dissociation of water into acidic hydronium ions ($H_3O^+$) and basic hydroxide ions ($OH^-$). In the subcritical region, the ionization constant ($K_w$) of water increases with temperature and is about three orders of magnitude higher than that of ambient water and the dielectric constant ($\in$) of water drops from 80 to 20. A low $\in$ allows subcritical water to dissolve organic compounds, while a high $K_w$ allows subcritical water to provide an acidic medium for the hydrolysis of biomass components. In addition, the physical properties of water, such as viscosity, density, dielectric constant and ionic product, can be tuned by changes in temperature and/or pressure in the subcritical region. Subcritical water offers several advantages over other biofuels production methods, including fast reactions (seconds to minutes), reduced mass transfer resistance, (v) ability to use mixed feedstock as well as wet biomass, and products are completely sterilized with respect to any pathogens including biotoxins, bacteria or viruses.

Figure 4:
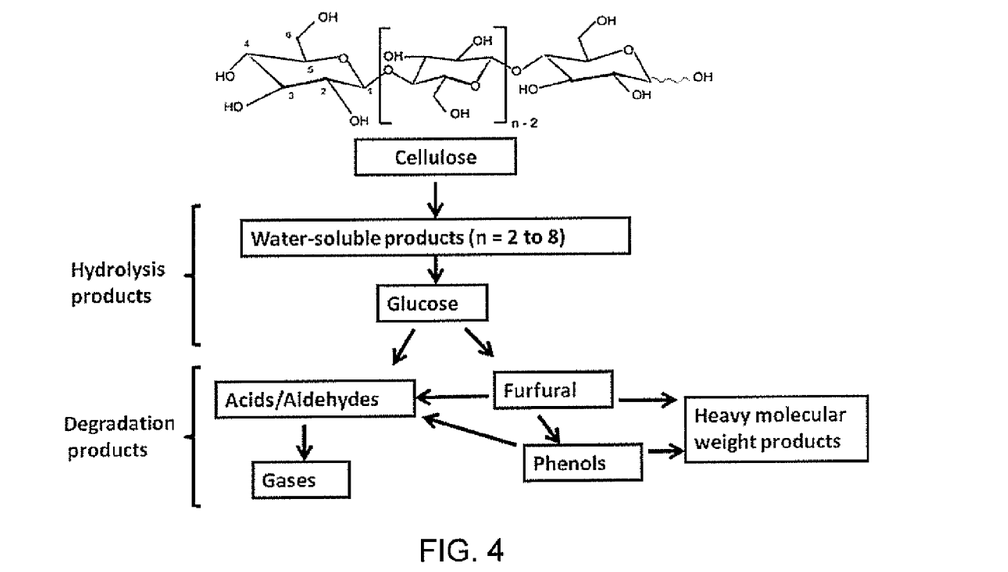
FIG. 4 is a simplified reaction schematic of cellulose in subcritical water.

Several experimental studies have been conducted on celluloses' and other carbohydrates' hydrolysis in subcritical water. The results showed that cellulose can be effectively converted to hydrolysis products (i.e., oligosaccharides, cellobiose and glucose) in order of a few seconds, as shown in FIG. 4. The degradation products can be stopped/minimized by optimizing the residence time and temperature. This eliminates the need of expensive enzymes (cellulase and hemicellulases) to hydrolyze carbohydrates conventionally used in enzymatic hydrolysis processes. On a larger scale, the disclosed process helps in developing compact hydrolysis reactors with higher throughput with a very fast reaction time. This is unlike enzymatic hydrolysis which can take several hours to days for achieving the similar fermentable sugar yields from carbohydrates.

The application of subcritical water as organic solvent in biofuels will help in replacing the use of corrosive and costly chemicals and realizing the benefits of chemicals-free green processes for producing biofuels.

The subcritical water hydrolysis method can be applied for nicotine extraction from the tobacco biomass. This requires tuning of temperature and residence times of the hydrolysis process. Nicotine extraction in aqueous phase can be up to 6.3 mg/g of dry tobacco biomass in a batch reactor. When a continuous reactor was used for the tobacco biomass hydrolysis at temperature in the range of 180-305° C. and residence times in the range of 10-15 seconds, the nicotine extraction was 0.6 mg/g of dry tobacco biomass. The yield of nicotine extraction can be changed by tuning the residence time and temperature under subcritical water conditions. Nicotine was analyzed by using high pressure liquid chromatography (HPLC) system equipped with a C18 column.

In subcritical water based processes, water is kept in liquid phase by applying pressure. Thus, latent heat required for phase change of water from liquid to vapor phase (2.26 MJ/kg of water) is avoided. This reduces the energy requirement compared to steam based processes. As an example, 2.869 MJ/kg of energy is required to convert ambient water to steam at 250° C. and 0.1 MPa whereas only 0.976 MJ/kg (about $\frac{1}{3}^{rd}$) of energy is required to convert ambient water to subcritical water at 250° C. and 5 MPa. This also means that the energy contained in the subcritical water is insufficient to vaporize the water on decompression. Further, it is possible to recover much of the heat ($>\frac{2}{3}^{rd}$) from subcritical water. A separate biomass drying step leads to large parasitic energy losses that can consume much of the energy content of the biomass. Therefore, biomass that has high moisture content (e.g. tobacco leaves) are highly desirable for reducing the energy intensive drying cost. Some of the advantages of the disclosed process include:

i. Freshly-cut tobacco biomass can be used to prepare feedstock for hydrolysis (no need of drying)
ii. Sugars and oil present in tobacco biomass can be phase separated after the hydrolysis.
iii. Feasible to design a compact satellite type reactor that can be installed in a field or near to the tobacco biomass source.
iv. No use of chemicals except water for the sugar hydrolysis from tobacco biomass.
v. Ability to extract nicotine in aqueous phase by tuning the temperature and residence time under subcritical water medium.

Figure 5:
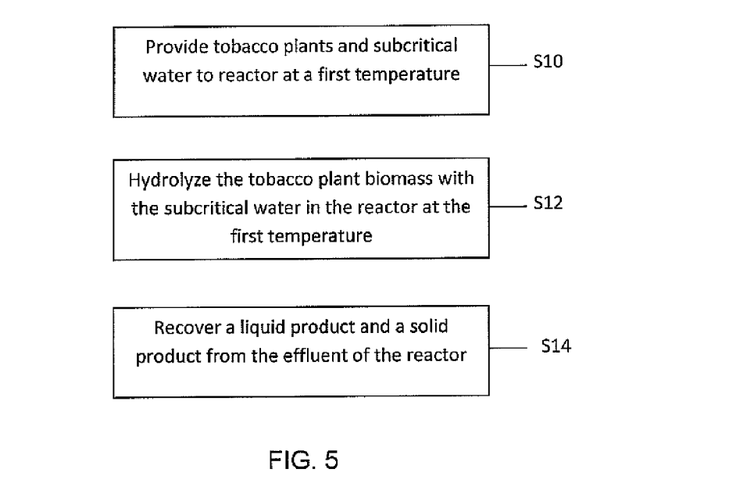
FIG. 5 is a flow diagram of a process disclosed herein.

The processing parameters below are illustrated below:
Operating Temperature Range 150 to 350° C.
Operating Pressure Range 200 psi to 3200 psi
Residence Time Range 5 seconds to 15 minutes
Heating Rate Rapid (similar to Flash Pyrolysis operation)
Feedstock Tobacco plant/leaves/stems/stalks/cured or other/mixed biomass FIG. 5 is a flow diagram of a process for fractionating carbohydrates and lipids or oils in tobacco plants as disclosed herein. The process fractionates water-soluble sugars and nicotine into a liquid product and lipids and oils into a solid product that can be further processed to produce biofuel oils. In step S10, a biomass of tobacco plants and subcritical water is provided at a first temperature to a reactor. The biomass can be the tobacco plant, the tobacco leaves, or the tobacco stems and stalks, as examples. The tobacco biomass can be wet-ground with or without water, i.e., chopped, mashed or otherwise agitated. The tobacco biomass can be mixed with other lignocellulosic feed stocks. The biomass and subcritical water can be premixed prior to being fed to the reactor or can be fed separately to the reactor.

In step S12, the biomass of tobacco plants is hydrolyzed with the subcritical water at the first temperature in the reactor. The first temperature can be between 150° C. and 350° C., and more particularly between about 170° C. and 305° C. The reactor can be pressurized to between about 200 psi and 3200 psi. Residence time in the reactor can be from about five seconds to about 30 minutes, and more particularly about five seconds and less than 15 minutes.

In step S14, a liquid product and a solid product are recovered from the reactor effluent, wherein the liquid product contains water-soluble sugars and nicotine. Oil can be extracted from the solid product in a further process step. In this process, greater than 70 wt % of the solids in the tobacco plants is converted to liquid product.

To optimize the recovery of nicotine in the liquid product, hydrolyzing can be performed in an acidic environment by feeding to the reactor an acid such as sulfuric acid, as a non-limiting example. A residence time of between 1 minute and 10 minutes also optimizes nicotine recovery. A residence time between 5 and 30 seconds optimizes sugar recovery. The process hydrolyzes the tobacco plant feed stock in the absence of cellulose enzymes.

As noted above, the process can also be performed in a two stage reaction process, recovering liquid product after each stage. The first stage temperature can be between about 150° C. and 200° C. and the second stage temperature can be between about 270° C. and 350° C.

The following sections present the results of example studies conducted to hydrolyze sugars from tobacco biomass:

Part 1: Single-stage continuous subcritical water reactor and the residence time was maintained of the order of few seconds
Part 2: Two-stage batch reactor and residence time of the order of few minutes in both the stages was used for the two-stage sugar hydrolysis approach.
Part 3: Subcritical water hydrolysis of tobacco stalks in batch reactor using one-stage sugar hydrolysis approach.
Part 4: Subcritical water hydrolysis of tobacco stalks in batch reactor using one-stage sugar hydrolysis approach assisted with diluted sulfuric acid addition.

EXAMPLE PART I

For subcritical water hydrolysis of tobacco leaves in a continuous flow reactor, the objective is to develop a subcritical water-based process for hydrolyzing sugar components of tobacco leaves (sample code: TB-Oil) in liquid phase. In order to hydrolyze the maximum amount of sugars from the tobacco leaves biomass in liquid phase, a set of experiments were performed at varying residence time and temperature in a continuous flow reactor as described below in Table 1. Residence time calculation for the continuous reactor:

$$t = \frac{V}{F\left(\frac{\rho_{pump}}{\rho_{P1,T1}}\right)}$$

Where V is reactor volume; F is the combined volumetric flow rate of pumps 1 and 2; ρ pump is the density of water at pump condition; and $\rho_{P1,T1}$ is the density of water at reactor condition ($T_1$ and $P_1$).

TABLE 1

Process parameters.

| Run | Temperature (° C.) | Residence time (seconds) |
|---|---|---|
| Exp 1 | 200 | 10 |
| Exp 2 | 200 | 15 |
| Exp 3 | 250 | 10 |
| Exp 4 | 250 | 15 |
| Exp 5 | 305 | 10 |

Figure 6:
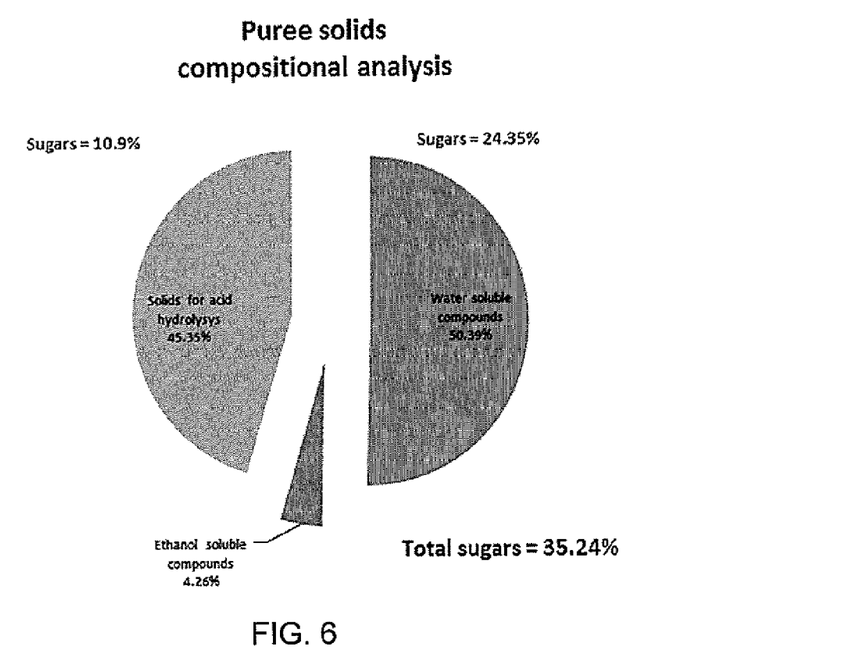
FIG. 6 is a graph of the compositional analysis (DW % basis) of tobacco biomass used for tobacco puree.

For all five experiments, a tobacco leaves (sample code: TB-Oil) puree was used. To obtain a uniform and more flowable material, additional water was added to the tobacco leaves. The prepared puree measured as 4.33 wt % solids. All the experiments were conducted at a constant pressure of 2000 psi. After dilution with preheated water, the solids load in the reaction zone is 0.62 wt %. The compositional analysis was performed and the results are shown in FIG. 6.

After the experiments, solid and liquid products were recovered. The liquid product was analyzed for pH, total organic carbon (TOC) and total nitrogen (TN). The absolute values are shown in the Table 2.

TABLE 2

Products analyses after the subcritical water hydrolysis.

| Sample | pH | TOC (mg/L) | TN (mg/L) |
|---|---|---|---|
| Exp 1 | 6.9 | 832 | 32.8 |
| Exp 2 | 6.9 | 1092 | 35.2 |
| Exp 3 | 6.7 | 1236 | 46.1 |
| Exp 4 | 6.4 | 1480 | 62.4 |
| Exp 5 | 6.2 | 1580 | 77.4 |

The solid product was also recovered and weighted in order to quantify the amount of solids converted to liquid and gaseous products as shown in Table 3.

TABLE 3

Conversion of tobacco biomass after subcritical water hydrolysis.

| Sample | Solids loaded (g) | Solids recovered (g) | % Conversion |
|---|---|---|---|
| Exp 1 | 2.71 | 1.262 | 41.7% |
| Exp 2 | 2.71 | 0.912 | 57.8% |
| Exp 3 | 2.71 | 0.782 | 63.8% |
| Exp 4 | 2.71 | 0.721 | 66.7% |
| Exp 5 | 2.71 | 0.707 | 67.3% |

The results show that biomass conversion increased with the temperatures and the residence time.

The elemental analysis for the tobacco biomass sample is: % C=37.12%, % N=5.08%, % H=4.97%. According to the elemental analysis information, the amount of C and N converted into liquid products is calculated and the results are shown in the Table 4.

TABLE 4

Conversion based on TOC and TN basis after subcritical water hydrolysis.

| Sample | % C conversion to liquid products | % N conversion to liquid products |
|---|---|---|
| Exp 1 | 55.4 | 15.9 |
| Exp 2 | 55.4 | 13.0 |
| Exp 3 | 67.8 | 18.5 |
| Exp 4 | 73.0 | 22.5 |
| Exp 5 | 85.3 | 30.5 |

In a similar way that the amount of biomass converted to liquid and/or gaseous products increases, the percentage of carbon and nitrogen being extracted/liquefied increased. Table 5 shows the percentage of sugars hydrolyzed during the experiments.

TABLE 5

Percentage of sugar hydrolyzed in liquid phase based on the initial dry biomass sugar content (35.23 wt % sugar in biomass) after subcritical water hydrolysis.

| | DNS sugars (mg/L) after Sulfuric Acid Hydrolysis | wt % extracted from total quantified sugar in biomass |
|---|---|---|
| EXP 1 | 461 | 32.35% |
| EXP 2 | 650 | 34.76% |
| EXP 3 | 712 | 41.14% |
| EXP 4 | 750 | 38.99% |
| EXP 5 | 719 | 40.88% |

EXAMPLE PART II

For subcritical water hydrolysis of tobacco leaves in batch reactor using two-stage sugar hydrolysis approach, the objective is to develop a two-step process using subcritical water conditions to maximize the sugar extraction from tobacco biomass.

The original tobacco leaves (sample code: TB-Oil) was converted into puree, to do so a similar amount of water (weight basis) was added and put in a blender until a homogeneous paste-puree was obtained. The puree was analyzed for moisture content and the solids were used for compositional analysis in order to determine the amount of sugars in the biomass. The solids in the puree were determined gravimetrically by drying the sample at 65° C. for 48 hours. Table 6 shows the results for the moisture content in the sample. The compositional analysis results are earlier shown in FIG. 4.

TABLE 6

Solids in tobacco puree used for experiments

| Original sample weight | Weight after drying | Weight loss | % of solids in sample |
|---|---|---|---|
| 39.4 g | 2.12 g | 37.27 g | 5.42% |

Experimental setup: The two-stage subcritical water hydrolysis process was performed in a batch reactor with a volume of 500 mL. The first extraction was performed at 180° C. for 3 minutes (time to reach experiment temperature/preheating time 11 min). The reactor was loaded with 430 mL of puree (5.42% solids). After the first-stage hydrolysis a 50 mL sample was collected to measure the amount of solids. The rest of the solids and liquid collected were centrifuged to separate them. The liquid fraction was analyzed for sugars by dinitrosalicylic (DNS) colorimetric method after further diluted sulfuric acid hydrolysis to recover sugars as monomers. The addition of small quantity (≤0.45% v/v) of sulfuric acid in the reaction medium lowers the pH and thus promotes the hydrolysis of carbohydrate fraction into oligomeric and monomeric sugars. The recovered solids after the first-stage hydrolysis were loaded into the reactor and water was added to make a final volume of 360 mL. The temperature for the second-stage hydrolysis was set to 280° C. for 3 minutes (time to reach experiment temperature/preheating time 22 minutes).

The final product was cooled down, collected and centrifuged to separate liquid and solid fractions. The liquid fraction was analyzed for sugars by DNS colorimetric method. The solids recovered were dried, weighted and a compositional analysis was performed to quantify the residual sugar content in the biomass after the two step extraction. Table 7 shows the parameters used for the first-stage hydrolysis and the results.

TABLE 7

First-stage subcritical water hydrolysis step

| | |
|---|---|
| Temperature (° C.) | 180 |
| Volume puree loaded (mL) | 430 |
| Solids in puree | 5.42 wt % |
| Solids loaded (g) | 23.31 |
| Sugars loaded (g) | 8.21 |
| Sugars extracted (g) | 1.83 |
| Sugar extraction | 22.27 wt % |
| Solids recovered (g) | 10.18 |
| Solids liquefied | 56.32 wt % |

Table 8 shows the result after the second-stage hydrolysis step and the total of solids liquefied and sugars extracted in both steps.

TABLE 8

Second-stage subcritical water hydrolysis step and final residue analysis

| | |
|---|---|
| Temperature (° C.) | 280 |
| Volume loaded (mL) | 360 |
| Solids loaded (g) | 10.18 |
| Sugars extracted (g) | 1.72 |
| Sugar extraction 2$^{nd}$ step | 10.48 wt % |
| Solids recovered final residue (g) | 4.35 |
| Sugars in final residue (g) | 0.56 |
| Solids liquefied | 57.27 wt % |
| Total solids liquefaction (2 steps) | 81.34 wt % |
| Total sugars extracted in 2 steps (g) | 2.69 |
| Sugar hydrolysis % in 2 steps | 32.75% |

Figure 7:
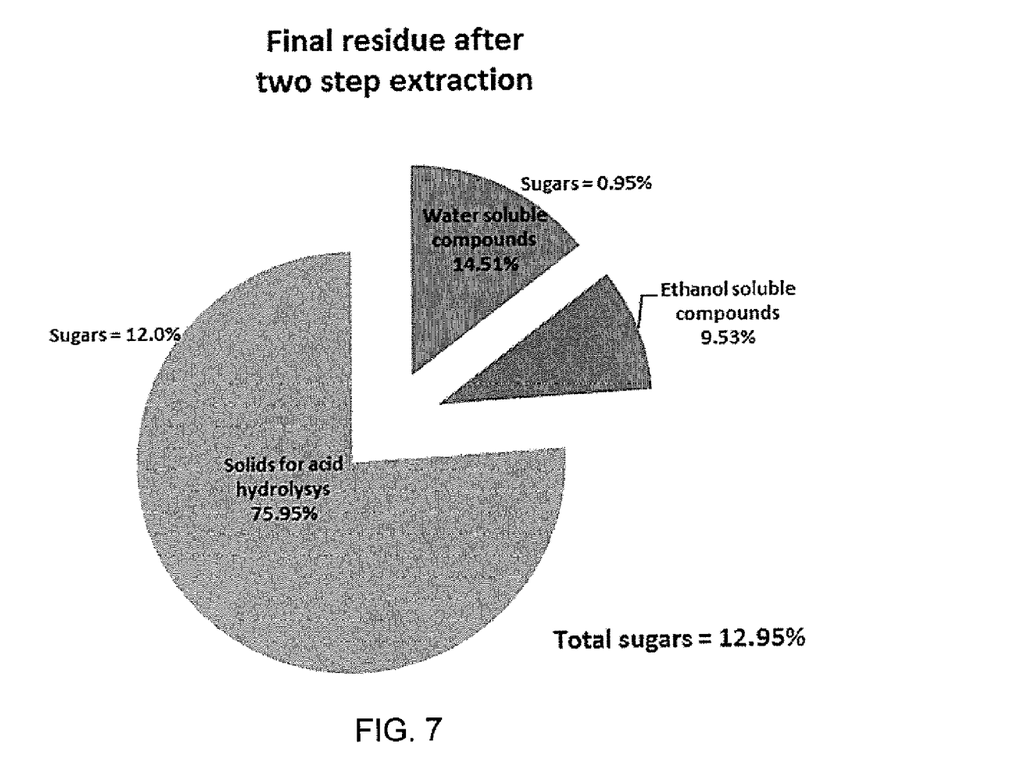
FIG. 7 is a graph of the composition (DW % basis) of a final residue after the two-stage subcritical water extraction.

The final residue collected was analyzed for the unhydrolyzed sugar content (compositional analysis) and FIG. 7 shows the results.

EXAMPLE PART III

Figure 8:
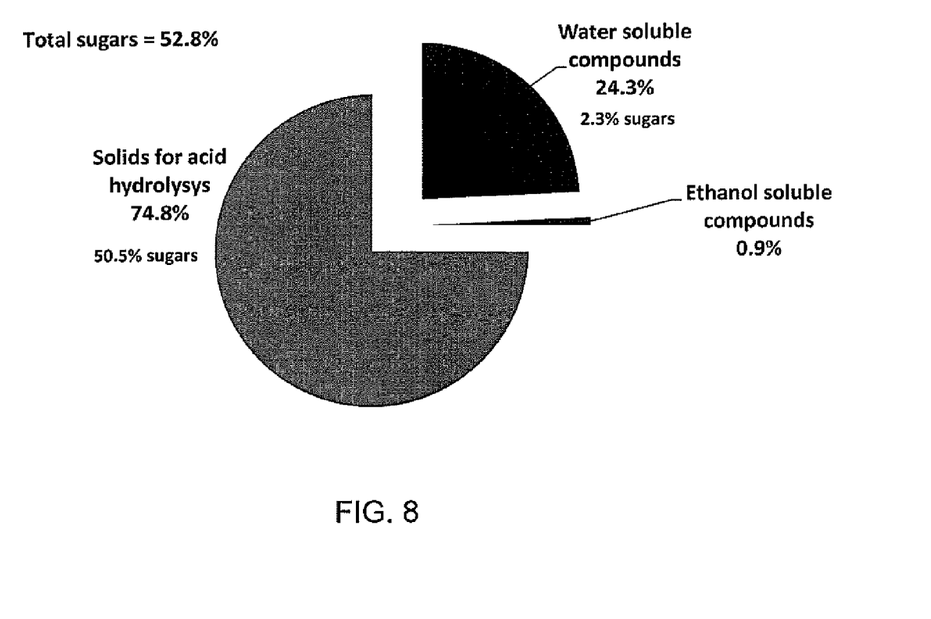
FIG. 8 is a graph of the composition (DW % basis) of tobacco stalk sample.

For subcritical water hydrolysis of tobacco stalks in a batch reactor using one-stage sugar hydrolysis approach, the objective is to develop a one-step process using subcritical water conditions to maximize the sugar extraction from tobacco stalks. The original tobacco biomass was dried (65° C. for 48 hours) and ground into small particles (>0.45 mm). The compositional analysis of the sample is shown in FIG. 8. The one step subcritical water hydrolysis process was performed in a batch reactor. The extraction was performed at 180° C. for 3 minutes. The reactor was loaded with 400 mL water and 40 g biomass powder sample. The extraction experiment was performed in duplicates; the times to reach experiment temperature are between 17 min and 14 mins. After the extraction all the sample was collected, separated solid fraction and liquid fraction by filtration method, collected liquid fraction and recorded liquid fraction volume, then used about 1000 mL pure water to rinse solid fraction and recorded rinsing water volume. The liquid fraction and rinsing water were analyzed for sugars by DNS method after further diluted sulfuric acid hydrolysis to recover sugars as monomers.

After 3 minutes of reaction time, 12.8% of the sugars were extracted (2.7 g from 21.01 g loaded). The sugar extraction is significantly lower than those experiments conducted using leaves as biomass sample. This is likely due to the harder structure or recalcitrant nature of mature tobacco stalks.

EXAMPLE PART IV

For subcritical water hydrolysis of tobacco stalks in a batch reactor using the one-stage sugar hydrolysis approach assisted with diluted sulfuric acid addition, diluted sulfuric acid was added to acquire acidic condition. A different volume of 72V/V % sulfuric acid ($H_2SO_4$) was added to pure water, with the total volume of liquid was 400 mL. The addition volume is shown in Table 9.

TABLE 9

Reaction conditions with diluted acid addition

| Reaction condition | Reagent | Addition Volume (mL) | Total Volume (mL) |
|---|---|---|---|
| 0.225 V/V% acidic condition | 72 V/V % H2SO4 | 1.25 | 400 |
| 0.45 V/V% acidic condition | 72 V/V % H2SO4 | 2.5 | 400 |

After the subcritical water hydrolysis, all the samples were collected, solid fraction and liquid fraction were separated by filtration method, the liquid fraction was collected and the liquid fraction volume was recorded. About 1000 mL pure water was used to rinse solid fraction and record rinsing water volume. The liquid fraction and rinsing water were analyzed for sugars. The solids recovered were dried, weighed and a biomass composition analysis was performed to quantify the residual sugar content in the biomass. The results are shown in Table 10.

TABLE 10

| Number | Acidic Con(%) | Reaction Time | Reaction Temperature ° C. | Sugar Loaded (g) | Total Sugar extraction (g) | Total Sugar extraction (%) | Pressure (psi) | Liquid Fraction pH |
| --- | --- | --- | --- | --- | --- | --- | --- | --- |
| 1 | 0.225% | 3 | 180 | 21.10 | 5.15 | 24.4 | 163 | 3.62 |
| 2 | 0.225% | 8 | 180 | 21.22 | 5.42 | 25.5 | 162 | 3.69 |
| 3 | 0.45% | 3 | 180 | 20.96 | 6.35 | 30.3 | 157 | 3.29 |
| 4 | 0.45% | 8 | 180 | 21.23 | 6.92 | 32.6 | 174 | 2.18 |

Based on the results of the example studies, it is observed that the solids conversion to liquid products is as high as 80 wt % during subcritical water hydrolysis whereas sugar yield were nearly 40 wt %. This indicates that parts of the hydrolyzed sugars are getting degraded to other organic compounds due to the longer residence time and higher temperature. The disclosed continuous process optimized with residence time in the range of few seconds under subcritical water conditions and in the temperature range of 150-350° C. is useful in preserving the sugars hydrolyzed from tobacco biomass puree. Nicotine extraction from tobacco biomass can also be achieved by subcritical water hydrolysis methods. A small amount (≤0.45% V/V) of sulfuric acid in the reaction medium can be used to increase the sugar yields from tobacco biomass hydrolysis.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A process for fractionating carbohydrates and lipids or oils in tobacco plants comprising:
    providing a biomass of tobacco plants and subcritical water at a first temperature to a reactor;
    hydrolyzing the biomass of tobacco plants with the subcritical water at the first temperature of greater than 180° C. and up to about 200° C., wherein the hydrolyzing of the biomass is essentially free of chemicals other than the subcritical water;
    recovering a liquid product and a solid product from the reactor, wherein the recovered liquid product contains water-soluble sugars and ranges in pH from 6.2 to 6.9;
    recycling the solid product to the reactor with subcritical water at a second temperature;
    further hydrolyzing the solid product with the subcritical water at the second temperature of greater than 280° C. and up to about 305° C., wherein the hydrolyzing of the solid product is essentially free of chemicals other than the subcritical water; and
    recovering a second liquid product and a second solid product from the reactor, wherein the second liquid product contains additional water-soluble sugars,
    wherein hydrolyzing occurs in an absence of cellulose enzymes.

2. The process of claim 1, further comprising:
    extracting oil from the second solid product.

3. The process of claim 1, wherein greater than 70 dried wt % of solids in the biomass of tobacco plants is converted to the first and second liquid products.

4. The process of claim 1, further comprising extracting oil from the solid product recovered from the hydrolyzing of the biomass of tobacco plants with the subcritical water at the first temperature.

5. The process of claim 1, wherein the biomass is prepared by wet-grinding the tobacco plants.

6. The process of claim 1, wherein hydrolyzing the biomass of tobacco plants with the subcritical water at the first and second temperatures is a continuous process.

7. The process of claim 1, wherein the continuous process has a residence time of 5 seconds to 15 minutes.

8. The process of claim 1, wherein the continuous process is integrated into a single reactor.

* * * * *